United States Patent [19]

Seagraves

[11] Patent Number: 5,003,105

[45] Date of Patent: Mar. 26, 1991

[54] PREPARATION OF 2-CHLOROTEREPHTHALOYL CHLORIDE

[75] Inventor: Robert L. Seagraves, Pennsville, N.J.

[73] Assignee: E.I. du Pont de Nemours and Company, Wilmington, Del.

[21] Appl. No.: 543,387

[22] Filed: Jun. 26, 1990

Related U.S. Application Data

[63] Continuation of Ser. No. 295,802, Jan. 10, 1989, abandoned.

[51] Int. Cl.$^5$ .............................................. C07C 51/58
[52] U.S. Cl. ..................................... 562/864; 562/866
[58] Field of Search .............. 562/864, 855, 493, 849, 562/856, 866

[56] References Cited

U.S. PATENT DOCUMENTS

3,833,652  9/1974  Knobloch ........................... 260/544
4,308,216 12/1981  Freitag et al. ...................... 260/544

FOREIGN PATENT DOCUMENTS

810595  3/1937  France .
1267055  6/1961  France .

OTHER PUBLICATIONS

Journal of Chemical Society, vol. 121, p. 2510 (1922).
Journal of the American Chemical Society, vol. 70, p. 3518 (1948).

Primary Examiner—Paul J. Killos
Assistant Examiner—Margaret Argo

[57] ABSTRACT

A process for preparing 2-chloroterephthaloyl chloride which comprises reacting terephthaloyl chloride with chlorine in the presence of an anhydrous ring chlorination catalyst. When the reaction mixture contains the desired amount of the monochloro product, the mixture is cooled to room temperature and the 2-chloroterephthaloyl chloride is isolated.

7 Claims, 1 Drawing Sheet

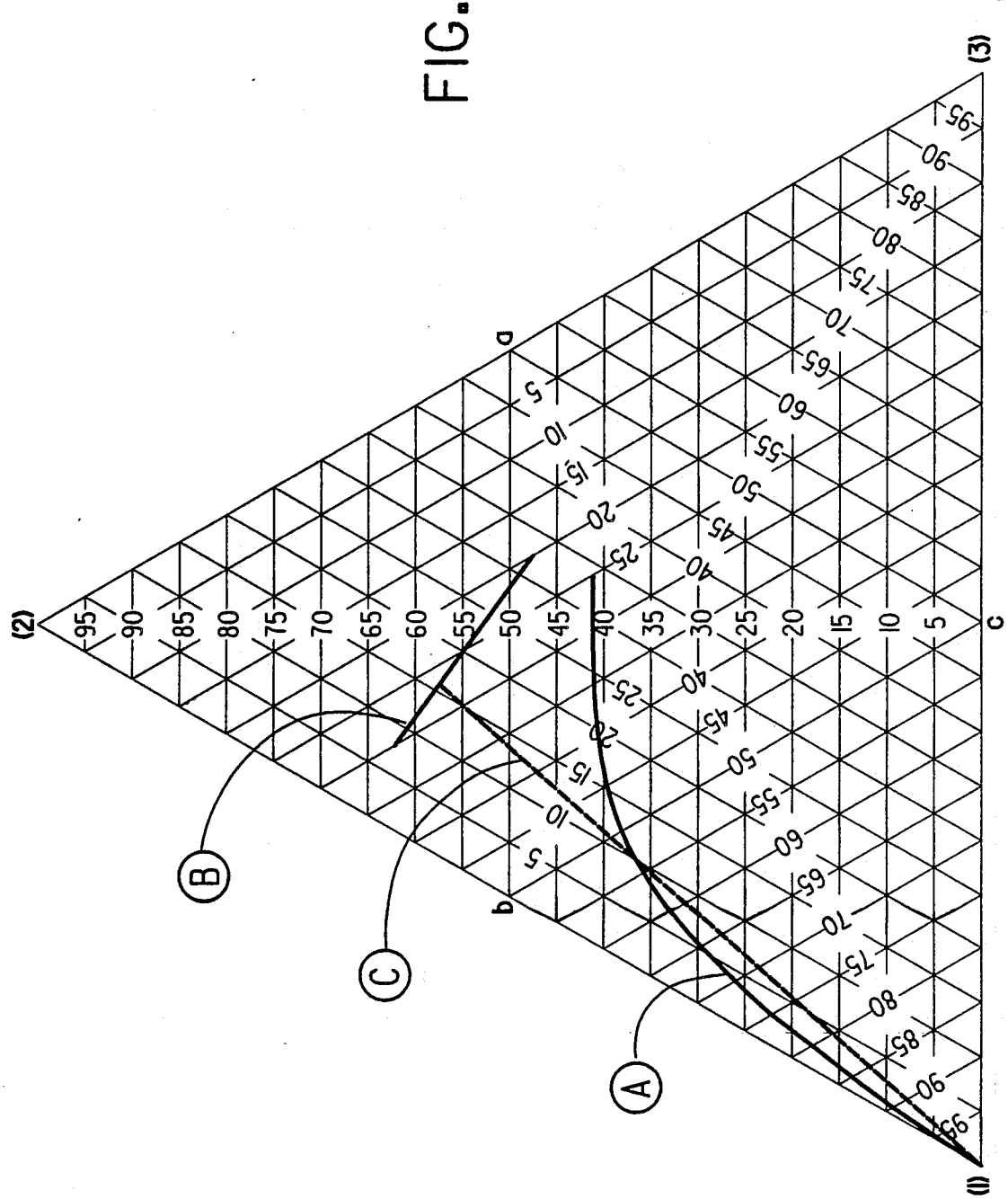

PREPARATION OF 2-CHLOROTEREPHTHALOYL CHLORIDE

This application is a continuation of application Ser. No. 07/295,802, filed Jan. 10, 1989, now abandoned.

BACKGROUND OF THE INVENTION

1. Field of the Invention

This invention relates to a process for the direct preparation of 2-chloroterephthaloyl chloride by the controlled chlorination of terephthaloyl chloride in the absence of a solvent, using ferric chloride as a catalyst.

2. Description of the Prior Art

The literature generally teaches several ways of producing 2-chloroterephthaloyl chloride. For example, French patent 810,595 issued Mar. 24, 1937 discloses the conversion of chloroterephthalic acid to chloroterephthaloyl chloride using the reagent thionylchloride. U.S. Pat. No. 4,308,216 issued Dec. 29, 1981 discloses the phosgenation of an aromatic acid such as chloroterephthalic acid to chloroterephthaloyl chloride. The starting compounds for these methods, chloroterephthalic acid, and it's precursor chloro-p-xylene are not available in commercial quantities and limit the utility of these methods for some applications.

The direct chlorination of terephthaloyl chloride in a solution of chlorosulfonic acid containing sulfur trioxide and an iodine catalyst is taught in the preparation of 2,3,5,6-tetrachloroterephthaloyl chloride. The monochloro component of that process is only formed in very minor amounts. See example 1, table 1 of U.S. Pat. No. 3,833,652 issued Sept. 3, 1974 on the application of Knobloch.

The monochlorination of benzoyl chloride is described in the Journal of Chemical Society, Vol. 121, p.2510 (1922). In that process, a steady stream of thoroughly dried chlorine is bubbled through benzoyl chloride with a small quantity of anhydrous ferric chloride. Benzoyl chloride has only one functional acid chloride group and as such is readily converted to the monochloride. In the Journal of the American Chemical Society, Vol..70, p. 3518(1948), isophthaloyl chloride was monochlorinated with ferric chloride catalyst at 95° to 100° C. and terephthaloyl chloride was chlorinated to the tetrachloro product. With isophthaloyl chloride, the first chlorine is substituted meta to both the acid chloride groups and the effect is to deactivate the ring further, thus high monochlorination is possible.

French patent 1,267,055 teaches ferric chloride as a chlorination catalyst in the preparation of dimethyl 2,3,5,6-tetrachloroterephthalate.

SUMMARY OF THE INVENTION

The present invention is a process for the preparation of 2-chloroterephthaloyl chloride which comprises placing molten terephthaloyl chloride in reactive contact with chlorine in the presence of an anhydrous ring chlorination catalyst for a time and temperature sufficient to produce a reaction mixture of about 30 to 41% by weight 2-chloroterephthaloyl chloride and preferably 35-38% 2-chloroterephthaloyl chloride.

The temperature of the reaction is maintained in the range 120°-180° C. and preferably in the range 140°-160° C. The reaction time is in the range of 8-17 hours and preferably for about 10 hours. In a preferred embodiment of this invention, the ring chlorination catalyst is ferric chloride present at greater than 0.1% by weight of the reaction mixture and more preferably, present at 0.5% by weight of the reaction mixture. Preferably the reaction mixture is allowed to cool, with agitation, to room temperature before separating the liquid and solid phases.

In the direct chlorination of terephthaloyl chloride, the first chlorine is substituted ortho to one of the acid chloride groups. The benzene ring is less deactivated than when benzoyl chloride and isophthaloyl chloride are chlorinated and hence the second chlorine goes on faster so the reaction proceeds rapidly to form polychlorinated products. Now there has been discovered, by the process of this invention a method to directly chlorinate the terephthaloyl chloride to yield useful quantities of the monochloro product, 2-chloroterephthaloyl chloride. In practicing the process of this invention, the dichloroterephthaloyl chloride is surprisingly produced in amounts of less than 25% by weight.

BRIEF DESCRIPTION OF THE DRAWING

FIG. 1 is a ternary diagram which shows the composition of the three components, (1) terephthaloyl chloride, (2) 2-chloroterephthaloyl chloride and (3) the sum of the dichloroterephthaloyl chloride isomers during the chlorination and in the mother liquor after melt crystallization of the reaction mixture. Line (A) represents the composition during chlorination of the total liquid reaction mixture, line (B) represents the liquid phase composition after crystallization of the reaction mixture and line (C) is a sample tie line.

DETAILED DESCRIPTION OF THE INVENTION

The source of the reactants for the present process is not particularly critical. Commercially available grades of terephthaloyl chloride and anhydrous ferric chloride are satisfactory. The ingredients should be kept anhydrous as the presence of moisture in the reactants lowers yields of the desired product.

The chlorination takes place over a reasonably wide temperature range. Acceptable yields of 2-chloroterephthaloyl chloride are achieved at temperatures in the range of 120°-180° C. and more preferably in the range 140°-160° C. At temperatures below the lower end of the range, the chlorination is too slow to be economical. Higher temperatures increase the reaction rate but degradation and control of the reaction limit the upper temperature. Temperature within the range of 120°-180° shows little or no effect on the proportion of the 2-chloroterephthaloyl chloride obtained.

In the conduct of the process of this invention, molten terephthaloyl chloride is contacted with chlorine in the presence of a ring chlorination catalyst for a period of 8-17 hours and more preferably about 10 hours. The longer time periods are associated with the lower chlorination temperatures. There exists a single phase (liquid) throughout the reaction.

The catalyst employed in this process is a typical ring chlorination catalyst and preferably anhydrous ferric chloride. Concentrations of greater than 0.1% ferric chloride, and preferably 0.5% by weight ferric chloride are employed. Lower concentrations of ferric chloride result in reaction times that are too long to be practical. The upper limit of ferric chloride present is set by ferric chloride's limited solubility in terephthaloyl chloride as undissolved ferric chloride is not effective as a catalyst.

The need for controlling the reaction period is evident from FIG. 1. The chlorination is stopped when the reaction mixture contains about 30 to 41% 2-chloroterephthaloyl chloride and preferably when the reaction mixture contains at most 35 to 38% 2-chloroterephthaloyl chloride. Beyond that point, the percentage of the dichloroterephthaloyl chloride increases rapidly while the percentage of the desired monochloro product increases very little. Once the 2-chloroterephthaloyl chloride has formed, there is a strong tendency for the reaction to proceed since 2-chloroterephthaloyl chloride chlorinates more readily than the starting material terephthaloyl chloride.

When the desired amount of 2-chloroterephthaloyl chloride has been obtained in the reaction mixture, the mass is allowed to cool, with agitation, to room temperature. During the cooling, crystals are formed. The solid phase which separates is rich in terephthaloyl chloride and is removed by standard separation devices such as a vacuum filter. These solids can be recycled to the reaction vessel with additional terephthaloyl chloride for further chlorination. The liquid filtrate contains up to 60% 2-chloroterephthaloyl chloride depending upon the 2-chloroterephthaloyl chloride in the reaction mass and the temperature at which the reaction mass is filtered. The 2-chloroterephthaloyl chloride in the filtrate can be purified by a series of distillations. A crude distillation, for example at 10 mm Hg through a 6" Vigreux column, removes ferric chloride and any high boiling by-products.

The 2-chloroterephthaloyl chloride product can be isolated from this distillate by batch or continuous vacuum distillation through a 50 tray Oldershaw sieve tray column or its equivalent. In the batch distillation, the first distillate contains terephthaloyl chloride with some 2-chloroterephthaloyl chloride product. This distillate can be recycled to the reaction vessel for further chlorination. The next distillate contains the desired product. The still bottoms from the distillation contain dichloroterephthaloyl chloride isomers and small amounts of product.

In the continuous vacuum distillation, two passes through the system are required. In the first pass, terephthaloyl chloride is taken off overhead with some product and the concentrated product is removed from the bottom of the column. In the second pass, the 2-chloroterephthaloyl chloride is removed overhead and the dichloroterephthaloyl chloride isomers containing some product are removed from the bottom of the column. In each case, the column bottoms are discarded. The product composition from the continuous vacuum distillation is greater than or equal to 96% 2-chloroterephthaloyl chloride, less than 4% terephthaloyl chloride and less than 0.5% dichloroterephthaloyl chloride isomers. In the batch distillation, the product cuts vary during the distillation. The product cuts combined would be the same quality as the continuous distillation.

The purity of the final product is measured by gas chromatography.

It is clear to one skilled in the art that the process of this invention can run continuously.

The 2-chloroterephthaloyl chloride produced by the process of this invention is useful as a monomer in preparing aromatic polyamides and other polymers such as polyester which can be used preparing fibers and films.

DESCRIPTION OF THE PREFERRED EMBODIMENTS

Example 1

In a 100 gallon glass-lined kettle equipped with agitator, condenser, temperature indicator, gas inlet tube into the liquid, condenser vented to a caustic scrubber, and heating or cooling medium to a jacket, was charged:

750 lb. Terephthaloyl Chloride, flaked
3 lb. Ferric Chloride, anhydrous

The terephthaloyl chloride was melted by applying low pressure steam to the jacket. The agitator was started and the mass heated to 135° C. Chlorine was fed into the liquid at a rate of 8-10 lb/hr for 15 hr. The composition of the mass, determined by gas chromatography, at that point was:

63% Terephthaloyl Chloride
31% 2-Chloroterephthaloyl Chloride
6% Dichloroterephthaloyl Chlorides The charge was cooled to 90° C., discharged into drums and cooled to ambient temperature over several days.

Upon cooling, the charge separated into liquid and solid fractions. 2-Chloroterephthaloyl chloride was concentrated in the liquid phase. The liquid was separated from the solid fraction. 301 lb. of liquid was recovered and had this composition determined by gas chromatography:

19% by weight Terephthaloyl Chloride
67% by weight 2-Chloroterephthaloyl Chloride
13% by weight Dichloroterephthaloyl Chlorides The filtrate was batch distilled under vacuum—first, through a 6" Vigreux column to remove ferric chloride and other high boilers and second, through a 50 tray Oldershaw column to separate 2-chloroterephthaloyl chloride from the lower boiling terephthaloyl chloride and the higher boiling dichloroterephthaloyl chlorides.

The yield based on the 2-chloroterephthaloyl chloride formed in the chlorination was 58%.

Example 2

In a 2 liter, round bottom, four neck flask equipped with electric mantle, agitator, thermometer, gas inlet tube into the liquid, and condenser vented to a caustic scrubber, was charged:

1377 gm. Terephthaloyl Chloride, molten @ 90°-100° C.
7 gm. Ferric Chloride, anhydrous The mass was agitated and heated to 150° C. Chlorine was added at 165 cc/min into the liquid over a ten hour period while maintaining the temperature at 140°-150° C. The composition, determined by gas chromatography, at that point was:

57% by weight Terephthaloyl Chloride
30% by weight 2-Chloroterephthaloyl Chloride
13% by weight Dichloroterephthaloyl Chlorides The mass was cooled to room temperature without agitation. The mass crystallized and was filtered to yield:

577 gm. solid phase
606 gm. liquid phase = 405 cc.

The liquid phase composition, determined by gas chromatography, was:

25% Terephthaloyl Chloride
60.5% 2-Chloroterephthaloyl Chloride
14.5% Dichloroterephthaloyl Chlorides The liquid phase was cooled to 8° C and filtered again. This yielded 524 gm.=350 cc. whose composition was:
17% Terephthaloyl Chloride
66% 2-Chloroterephthaloyl Chloride
17% Dichloroterephthaloyl Chlorides

I claim:

1. A process for the preparation of 2-chloroterephthaloyl chloride which comprises:
   (a) placing molten terephthaloyl chloride in reactive contact with chlorine in the presence of ferric chloride as an anhydrous ring chlorination catalyst for a time and temperature sufficient to produce a reaction mixture of about 30 to 41% by weight 2-chloroterephthaloyl chloride;
   (b) cooling the reaction mixture containing about 30 to 41% by weight 2-chloroterephthaloyl chloride to at least as low as room temperature, thereby causing a crystallization of solid terephthaloyl chloride;
   (c) removing the crystallized terephthaloyl chloride from the reaction mixture;
   (d) distilling terephthaloyl chloride from the reaction mixture; and
   (e) distilling 2-chloroterephthaloyl from the reaction mixture.

2. The process of claim 1 wherein the temperature is maintained in the range 120°-180° C. and for a time in the range of 8-17 hours.

3. The process of claim 1 wherein the temperature is maintained in the range 140°-160° C. and for a time of about 10 hours.

4. The process of claim 1 wherein the reaction mixture produced is in the range of 35 to 38% by weight 2-chloroterephthaloyl chloride.

5. The process of claim 1 wherein the catalyst is present at greater than 0.1% by weight of the reaction mixture.

6. The process of claim 1 wherein the catalyst is present at about 0.5% by weight of the reaction mixture.

7. The process of claim 1 wherein the reaction mixture is allowed to cool to room temperature.

* * * * *